United States Patent
Gill

(10) Patent No.: US 12,102,788 B2
(45) Date of Patent: Oct. 1, 2024

(54) PORTABLE IV BAG SUSPENSION DEVICE

(71) Applicant: Stacey L. Gill, Seattle, WA (US)

(72) Inventor: Stacey L. Gill, Seattle, WA (US)

( * ) Notice: Subject to any disclaimer, the term of this patent is extended or adjusted under 35 U.S.C. 154(b) by 94 days.

(21) Appl. No.: 17/992,740

(22) Filed: Nov. 22, 2022

(65) Prior Publication Data
US 2024/0165323 A1    May 23, 2024

(51) Int. Cl.
*A61M 5/14*    (2006.01)

(52) U.S. Cl.
CPC ..... *A61M 5/1415* (2013.01); *A61M 2209/082* (2013.01)

(58) Field of Classification Search
CPC .......... A61M 5/1415; A61M 2209/082; A47G 25/0614; A47G 25/08; F16B 45/00; F16B 45/005; B65D 63/10
USPC ....... 248/323, 300–301, 304, 308, 339, 215, 248/317, 693; 224/309, 324, 482; 24/302
See application file for complete search history.

(56) References Cited

U.S. PATENT DOCUMENTS

| | | | |
|---|---|---|---|
| 1,726,316 A * | 8/1929 | Saxton | A47G 25/08 33/8 |
| 2,605,906 A * | 8/1952 | Pontius | A47G 25/08 D6/323 |
| 2,938,696 A | 5/1960 | Hinshaw | |
| 3,966,160 A | 6/1976 | Wilson | |
| 4,325,528 A | 4/1982 | Martin | |
| 4,763,820 A * | 8/1988 | Gardner, Jr. | B60R 7/10 224/927 |

(Continued)

FOREIGN PATENT DOCUMENTS

| | | |
|---|---|---|
| CN | 308635317 | 5/2024 |
| KR | 3008122030000 | 8/2015 |
| KR | 3012568120000 | 4/2024 |

OTHER PUBLICATIONS

National Hardware Over the Door Robe Hook, National Hardware, [Post date: unknown], [Site seen: Jun. 12, 2024], Seen at URL: https ://www.build.com/producUsu m mary/ 1934988?uid=457344 7 &j mtest=gg-gbav2_ 457344 7 &inv2= 1&&source=gg-gba-pla_ 457344 7! c1674295608!a6%E2%80%A6 (Year: 2024).

(Continued)

*Primary Examiner* — Ingrid M Weinhold
(74) *Attorney, Agent, or Firm* — Bamert Regan PLLC; Michael J. Folise, Esq.

(57) ABSTRACT

A portable IV fluid bag suspension device has a flexible main body defined by a slender, elongated strap having inner and outer surfaces. The inner surface is provided with two pockets on opposite sides of a tab defining a grommet or a hole for receipt of a hook or the like from an intravenous fluid bag. A stiffening member having two legs disposed at an acute angle has first and second legs which reside in the first and second pockets on the main body so as to provide rigidity to the flexible main body. A second tab is provided adjacent an end of the strap distal from the first tab which may be inserted behind a door or a drawer such that when the door or drawer is closed, the structure is capture by the door or drawer and the first tab is rigidly defined in a space relationship from a front surface of the door or drawer whereby the intravenous fluid bag may be hung therefrom without interference from the support structure.

20 Claims, 2 Drawing Sheets

(56) References Cited

U.S. PATENT DOCUMENTS

| | | | |
|---|---|---|---|
| 4,889,268 A * | 12/1989 | Shubeck | G09F 21/04 |
| | | | 211/89.01 |
| D308,099 S | 5/1990 | Jimenez | |
| D315,862 S | 4/1991 | Specker, Jr. | |
| 5,246,190 A * | 9/1993 | Swirkal | B60K 35/50 |
| | | | 224/567 |
| D365,015 S | 12/1995 | Avinger | |
| D445,669 S | 7/2001 | Goodman et al. | |
| 6,364,260 B1 * | 4/2002 | Lorincz | A47B 96/06 |
| | | | 211/113 |
| 6,412,675 B1 * | 7/2002 | Pope | B60R 9/02 |
| | | | 224/325 |
| D548,065 S | 8/2007 | Zhu et al. | |
| D635,846 S | 4/2011 | Klein et al. | |
| 8,333,448 B2 | 12/2012 | Yoon et al. | |
| 8,499,941 B2 | 8/2013 | Barkdoll et al. | |
| 8,567,738 B1 | 10/2013 | Adair | |
| 9,642,778 B1 | 5/2017 | Yazbeck | |
| D811,205 S | 2/2018 | Hanley | |
| D858,261 S | 9/2019 | Gong | |
| 11,427,132 B2 * | 8/2022 | Woodard | B60R 7/10 |
| D1,005,826 S | 11/2023 | Pimentel | |
| 2004/0182976 A1 | 9/2004 | Valiulis et al. | |
| 2008/0235914 A1 * | 10/2008 | Dolberg | B60N 3/026 |
| | | | 16/110.1 |
| 2012/0118650 A1 | 5/2012 | Gill | |
| 2013/0066155 A1 | 3/2013 | Keating et al. | |
| 2016/0091121 A1 * | 3/2016 | Mackie | H02G 3/32 |
| | | | 29/432 |
| 2016/0262555 A1 | 9/2016 | Boehnen et al. | |
| 2024/0165323 A1 | 5/2024 | Gill | |

OTHER PUBLICATIONS

TICONN 13/64" Z Shape Shelf Bracket, Metal Shelf Brackets, TICONN, Amazon.com, [Post date: Sep. 9, 2022], [Site seen: Jun. 12, 2024], Seen at URL: https://www.amazon.com/TICONN-Heavy-Duty-Shelf-BrackeUdp/BOBDRHY7N6/ref=sr_1_243_sspa (Year: 2022).

* cited by examiner

PORTABLE IV BAG SUSPENSION DEVICE

CROSS REFERENCE TO RELATED APPLICATION(S)

This non-provisional application is related to U.S. Patent Application Pub. No. 2012/0118650, entitled DEVICE FOR POSITIONING A CONTAINER FOR A GRAVITY-FED INTRAVENOUS FLUID DELIVERY SYSTEM, published May 17, 2012, the entirety of which is incorporated herein by reference. No claim of domestic priority is being made.

FIELD OF THE INVENTION

The invention relates generally to suspension systems for intravenous fluid bags, and, more particularly, to portable fluid medicament bag suspension systems.

BACKGROUND OF THE INVENTION

Gravity-fed intravenous fluid delivery systems (commonly referred to as an "IV Drip") utilize gravity to deliver fluid from a suspended container to a location that is positioned lower than the container of fluid. Typically, the delivery location is a human being's circulatory system, hence the term "intravenous" wherein a needle is positioned in a vein on a person's arm or leg wherein substances are delivered directly into a vein. Therapies administered intravenously are often called specialty pharmaceuticals and may be commonly referred to as a drip because many systems of administration employ a drip chamber (e.g., a suspended container), which prevents air entering the blood stream (air embolism) and allows an estimate of flow rate. Intravenous therapy may be used to correct electrolyte imbalances, to deliver medications, for blood transfusion or as fluid replacement to assist with, for example, dialysis. Compared with other routes of administration, the intravenous route is a fast way to deliver fluids and medications throughout the body.

With rising healthcare costs, more and more treatments are being performed on an outpatient basis rather than an inpatient basis. Typical medical procedures which now may be performed on an outpatient basis include rehydration of patients suffering from diabetes mellitus and peritoneal dialysis in which the peritoneal cavity is used as a fluid retention reservoir to perform dialysis without the necessity of a dialysis machine. Such procedures must be performed three to four times per day on an ongoing basis. Thus, a conventional suspended intravenous pole, typically on wheels, may not be suitable for use in the home environment or for travel. With a suspended container, a conventional manner of suspending the container may be using an IV drip stand. An IV drip stand may include a base that supports a pole that extends high enough in a vertical direction such that a suspended container may be suspended higher than the intravenous injection point in the person receiving therapy. The IV stand, however, is cumbersome and bulky as it must necessarily be tall enough to suspend the fluid container higher than a person's arm or leg. Sometimes, one can wheel the IV stand around if the base has wheels. Further, sometimes, the IV pole may be mounted directly to a bed where the person must remain when receiving therapy. In these cases, a problem exists wherein the IV stand is less mobile in that the IV stand cannot be easily transported in a vehicle or airplane. An IV pole attached to a bed is worse for portability as very few vehicles or airplane can accommodate a hospital bed. Cumbersome and bulky IV stands are difficult to deal with when portability is needed.

Alternative to wheeled IV poles are disclosed in various prior references. Adair discloses a portable intravenous device and hanger therefore in U.S. Pat. No. 8,567,738, issued Oct. 29, 2013, directed to veterinary field calls. The device includes a bracket which may be secured to a structure, presumably a wall section or door. Nevertheless, the device is complex, expensive to manufacture and sell, and not well-suited for a temporary or occasional home use.

U.S. Pat. No. 3,966,160, issued on Jun. 29, 1976, to Wilson discloses an inflight intravenous bottle holder for use with stacked litters such as in a life flight aircraft. The device is adapted to be vertically adjustable on vertical poles which interconnect the various litters. Wilson's device is not suitable for home use.

My own device for positioning a container for a gravity fed intravenous fluid delivery system was disclosed and published in US patent application 2012/0118650, published on May 17, 2020, titled, "Device for Positioning a Container for a Gravity Fed Intravenous Fluid Delivery System" resolves many issues and limitations of the herein above discussed prior art references. My device described in said publication is a simple unitary structure having a leg portion which can reside against the back of a door and an integral leg portion which resides on top of the door, leading to an extended frame leg from which an intravenous fluid bag may be mounted. Although the device is inexpensive and relatively light weight, it is cumbersome and does not pack well for travel. An attempt to avoid and overcome these difficulties is shown in an alternative embodiment of the invention where the various legs are interconnected by hinges so as to make the device foldable. However, such hinges are expensive to manufacture and may compromise the rigidity of the device while holding e.g. an IV bag. The result of such a device collapsing while intravenous fluid is being administered is significant. It may be impossible to know at that point how much of a dose has been metered. Moreover, when the bag impacts e.g. the floor, air may be introduced into the intravenous fluid line connected to the patient resulting in a dangerous embolism. Therefore, a need exists for a portable intravenous fluid bag suspension device which is inexpensive to manufacture, highly portable, yet extremely rigid and resistant to collapse when suspending an intravenous fluid bag.

SUMMARY OF THE INVENTION

It is therefore an object of the present invention to provide for a fluid medicament bag suspension device which is extremely rigid and, yet, may be disassembled for easy transport. It is a further object of the invention to achieve the above object with the device which is inexpensive to manufacture and easy to assemble.

The invention achieves the above objects and advantages, as well as other objects and advantages that will become apparent from the description which follows by providing a portable fluid bag suspension device having an elongated strap, defining inner and outer surfaces, and first and second distal ends. The outer surface has a first tab extending therefrom intermediate the distal end and a second tab extending from one of the surfacing proximal to the second end and adapted to pass over a portion of a door or a drawer. The inner surface of the strap further has a first and second open end pockets positioned on opposite sides of the first tab for receiving a stiffening member having first and second legs disposed at an acute angle with respect to one another for respective receipt in the first and second pockets. An aperture is provided on the first tab for removal receipt of e.g., an IV bag. The legs of the stiffening member may be received in the corresponding pockets and the second tab placed behind a closed door or drawer so that the strap second distal end abuts an obverse side of the door or drawer. The received first leg will thus suspend the aperture on the first tab in free space away from the door or drawer, with the received second leg pressing against the exposed side of the door or drawer. In preferred embodiments of the invention, the stiffening member is removably received in the pockets so that when removed therefrom, the stiffening member may be conveniently packed in the corner section of a valise or a suitcase while the flexible main body may be adapted to any structure or items within the bag or valise. In the preferred embodiments of the invention, the acute angle on the stiffening member is in a range of approximately 40 to 60 degrees and preferably approximately 45 degrees. The main body is preferably manufactured from a flexible material such as textile and has an overall length of approximately 14.5 inches and a width of approximately two inches.

BRIEF DESCRIPTION OF THE DRAWINGS

Preferred and alternative embodiments of the present invention are described in detail below with reference to the following drawings.

DETAILED DESCRIPTION OF THE PREFERRED EMBODIMENT

A portable intravenous (hereinafter "IV") fluid bag suspension device in accordance with the principles of the invention is generally indicated at reference number 10 in the various Figures of the attached drawings, wherein numbered elements in the Figures correspond to like numbered elements herein. As used herein, the terms "IV fluid bag", "fluid medicament bag", "IV bottle" and the like refer to and mean any fluid medicament container which is inverted for gravity feed of the medicament fluid therein for use in association with medical treatments.

Figure 1:
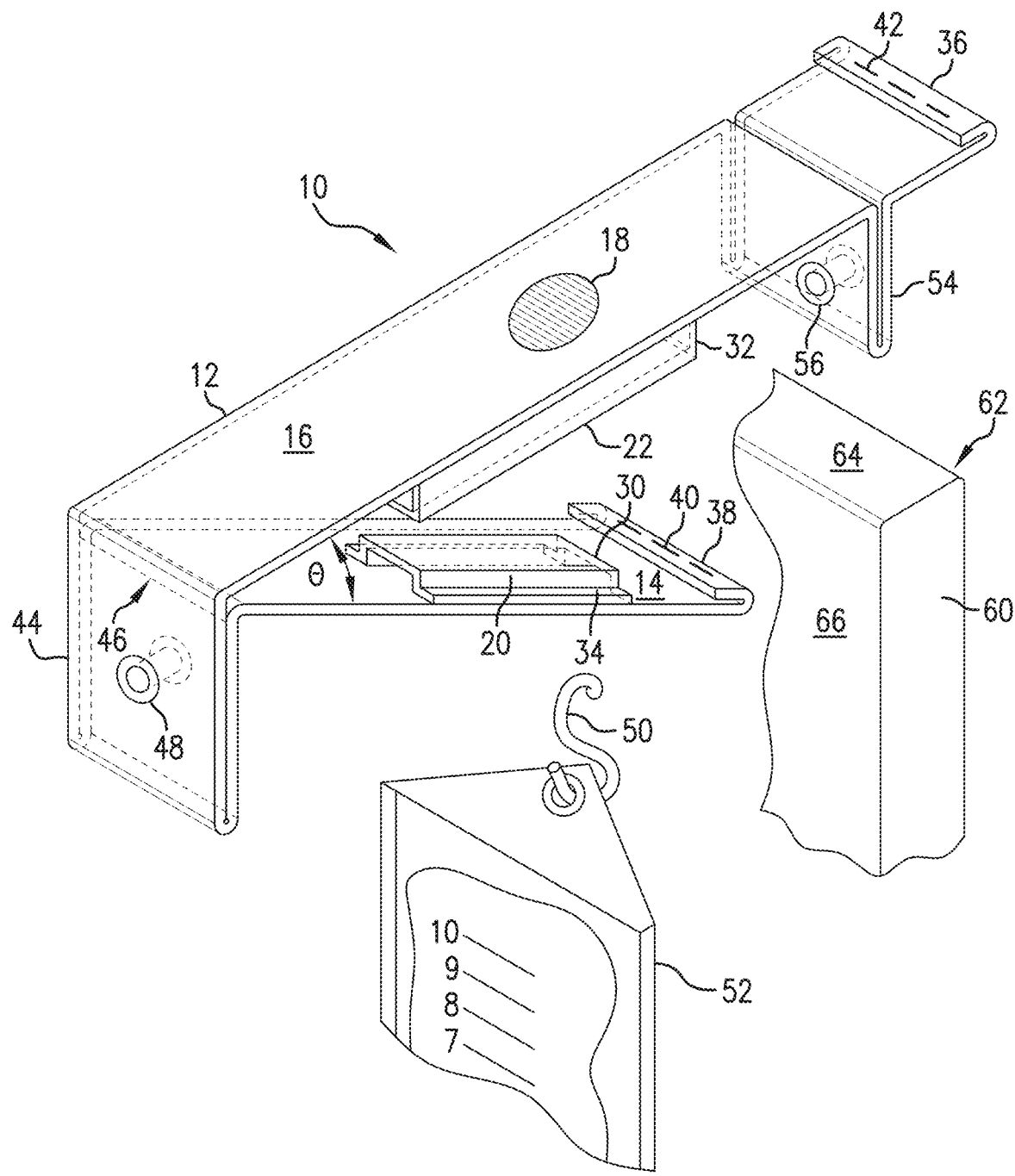
FIG. 1 is a top right perspective view of a portable medicament fluid bag suspension device in accordance with the principle of the invention showing the device adjacent to environmental structures such as a door upon which the device may be mounted and an intravenous fluid bag which may be attached to a tab on the device.
Figure 2:
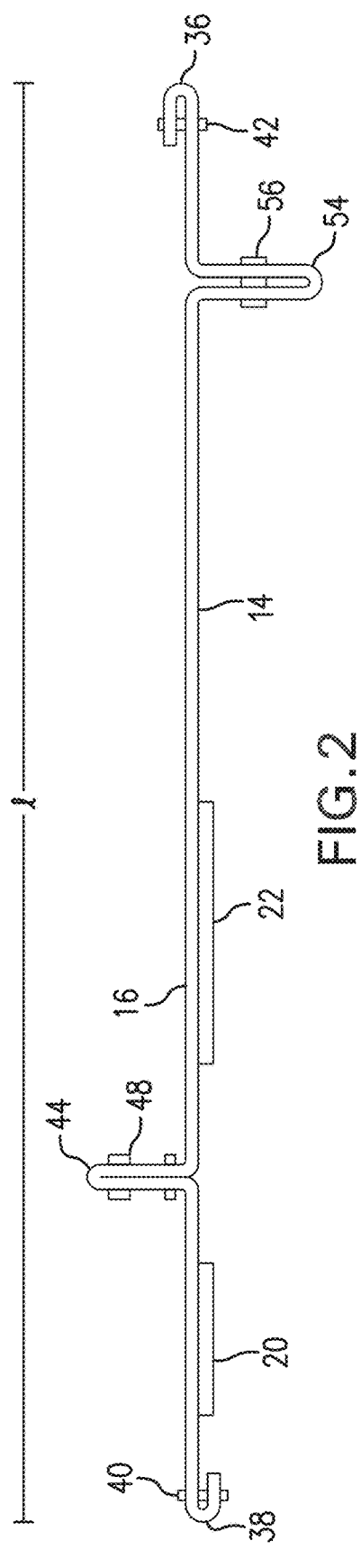
FIG. 2 is a right-side elevational view of the device shown in FIG. 1, the left side elevational view being a mirror image thereof.
Figure 3:
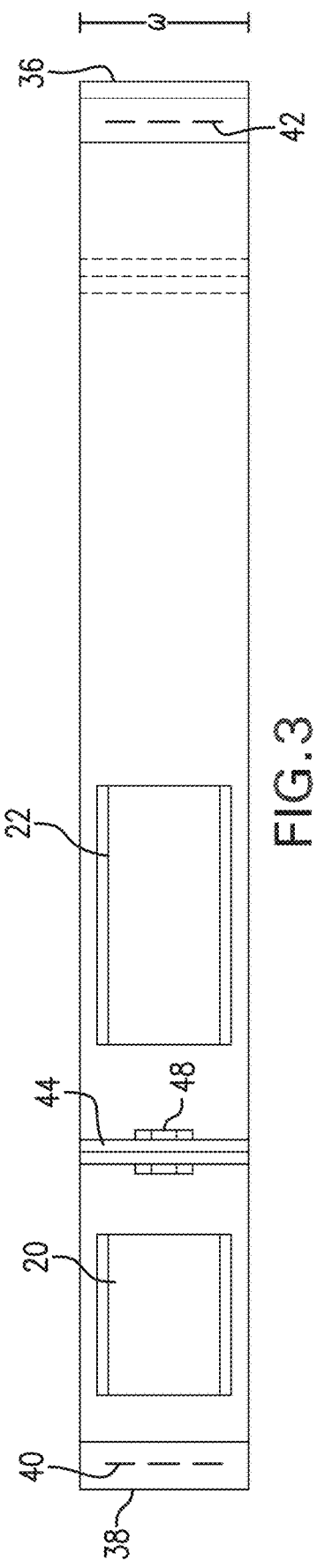
FIG. 3 is top plan view of the device shown in FIG. 2.
Figure 5:
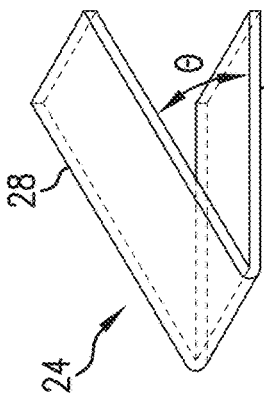
FIG. 5 is a top right perspective view of a stiffening member of the invention showing the angle Θ at which two legs of the member are disposed with respect to one another.
Figure 4:
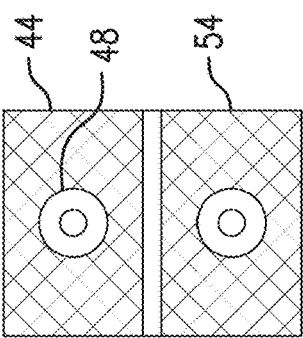
FIG. 4 is an end view of the device show in the Figures.

As best seen in FIG. 1, the device 10 has a flexible main body or strap 12 preferably manufactured from a textile material such as Nylon or Dacron® seatbelt webbing. The main body or strap 12 defines an inner surface 14 and an outer surface 16. Circled area 18 is cross-hatched to indicate that the material is woven and well preferably a synthetic material such as nylon or Dacron®. Other suitable materials having adequate tensile strength such as cotton duck may be substituted. As best seen in FIGS. 2 and 3, the strap has an overall length (l) of approximately 14.5 inches and a width (w) of approximately 2 inches. The inner surface 14 of the strap 12 has first and second pockets 20, 22 for receipt of a stiffening member generally indicated at reference numeral 24 in FIG. 5. The stiffening member has a first leg 26 and a second leg 28 disposed at an angle Θ for corresponding receipt in the first and second pockets 20 and 22 of the main body 12. The stiffening member 24 is preferably manufactured from a thermoplastic polymer material such as Acrylonitrile Butadiene Styrene (ABS) and the angle Θ is preferable between 40 and 60 degrees, and in the preferred embodiment is 45 degrees. The first and second pockets 20, 22 are shown as being open ended 30, 32 but may be closed ended. The pockets are loops of material which may be stitched to the main body such as by stitches 34. Free ends 36, 38 of the main body or strap 12 are formed by folding over the strap and stitching the ends thereof with stitches 40, 42. If the main body is formed from a synthetic material, the free ends may also be thermally welded to prevent unraveling. A first tab 44 is formed from the outer surface 16 of the main body by doubling over the strap and attaching the strap with stitches 46 so as to form a tab having a length of approximately 1 inch. A grommet 48 is formed in the first tab so as to accept a hook 50 of a conventional intravenous fluid bag 52. A linear weight scale (not shown) may be interposed between the IV bag 52 and the grommet 48 so that fluid in the bag may be metered by weight. A second tab 54 is formed adjacent to the distal free end 36 on the inner surface of the strap 12 in the preferred embodiment, and in a like manner to the first tab 44 by doubling over the strap and stitching. A second grommet 56 is provided therein for purposes which will be described herein below.

When received in the first and second pockets 20, 22 the first and second legs 26, 28 of the stiffening member 24 provides rigidity to the otherwise flexible main body 12. This permits the second tab 54 of the main body to be placed behind a door or drawer 60 such that the second tab 54 resides against an obverse side 62 of the door while a portion of the main body adjacent to the second tab 54 resides on a top portion 64 of said door. When the door or drawer is closed, the second tab 54 will be captured there behind, and the free end 38 will abut against a front surface 66 of the door or drawer when the door or drawer is closed. In this manner, the first tab 44 carrying the grommet 48 will be suspended in free space at least 4 inches away from the door allowing the intravenous fluid bag 52 to be suspended therefrom without touching the door. Such suspension of the bag in free space is important to the free flow of medicament within the bag through the VI tube (not shown) to the patient. Such free suspension is also important if a weight scale is used for purposes of metering the dose such that the weight is not partially carried by the front surface 66 of the door or drawer rendering an inaccurate weighing.

The suspension device 10 described above advantageously permits a user who may have to perform an outpatient procedure such as peritoneal dialysis three to four times per day with the opportunity to suspend the fluid medicament bag 52 from a hotel door or drawer while traveling. The stiffening member 24 is readily removed from the first and second pockets 20, 22 so that the stiffening member may be positioned in a corner of a suitcase or valise while the flexible main body 12 is folded up and neatly placed therein as well. The removable capability of the stiffening member 24 advantageously permits the main body 12 to be used in an alternate embodiment and method wherein the main body 12 is directly suspended from a coat hook or the like in a dwelling or hotel room without the use of the stiffening member. This may be the case where the main body is suspended far enough away from the wall or other support member by the coat hook or the like so that the fluid bag is relatively located in free space and not against a support. Specifically, the second tab 54 has means (grommet 56) for hanging the device 10 from a hook (not shown) without the stiffening member 24 received in the pockets 20, 22.

It should be apparent to those of ordinary skill in the art that modifications may be made to the preferred embodiment of the invention without deviating from the spirit and scope of the invention itself. For example, the second tab 54 may be constructed so as to be directed from the outer surface 16 of the main body 12 rather than the inner surface 14 as shown in FIGS. 1 through 4. Moreover, as should also be apparent from the above, the fluid delivery is not limited to intravenous, but may also be subcutaneous or any other medically appropriate delivery means or infusion method.

Thus, the invention is not to be limited by the above disclosure but determined in scope by the Claims which follow.

The invention claimed is:

1. A foldable portable fluid medicament bag suspension device, comprising:
    a flexible main body defined by a slender, elongated strap having inner and outer surfaces and first and second distal ends, a first tab formed by a folded over portion of the strap intermediate the distal ends, a second tab formed by a second folded over portion of the strap proximal to the second end, the first tab extending in a direction opposite the second tab when the strap is in an extended configuration, the inner surface having first and second open ended pockets positioned on opposite sides of the first tab;
    a stiffening member having first and second legs disposed at an acute angle with respect to each other for respective removable receipt in the first and second pockets; and
    means on the first tab for removable receipt of a fluid medicament bag,
    whereby the bag suspension device has a first suspension configuration in which the stiffening member can is adapted to be received in the pockets of the main body and the second tab is adapted to be passed over a top portion of a door or drawer that is then closed so that when so received the main body second distal end abuts an obverse side of the door or drawer so as to suspend the means on the first tab spaced away from the door or drawer.

2. The device of claim 1 wherein the main body is fabricated from a textile material.

3. The device of claim 2 wherein the textile material is continuous.

4. The device of claim 2 wherein the textile material is nylon webbing.

5. The device of claim 1 wherein the means on the first tab is a grommet.

6. The device of claim 1 wherein the acute angle is in a range of 40 to 60 degrees.

7. The device of claim 6 wherein the acute angle is approximately 45 degrees.

8. The device of claim 1 wherein the main body has a length of approximately 14.5", a width of approximately 2", and the tabs have a length of approximately one inch each.

9. The device of claim 8 wherein the first leg of the stiffening member has a length of approximately 4" and the second leg has a length of approximately 6".

10. The device of claim 1 wherein the second tab has means for alternatively hanging the device in a second suspension configuration, in which the second tab is hung from a hook without the stiffening member received in the pockets.

11. A foldable portable fluid medicament bag suspension device, comprising:
    an elongated strap having inner and outer surfaces and first and second distal ends, a first tab formed by a folded over portion of the strap intermediate the distal ends, a second tab formed by a second folded over portion of the strap proximal to the second end, the first tab extending in a direction opposite the second tab when the strap is in an extended configuration, the inner surface having first and second open ended pockets positioned on opposite sides of the first tab;
    a stiffening member having first and second legs disposed at an acute angle with respect to each other for respective receipt in the first and second pockets; and
    an aperture defined by the first tab for removable receipt of a fluid medicament bag,
    whereby the bag suspension device has a first suspension configuration in which the legs of the stiffening member is adapted to be received in the pockets and the second tab is adapted to be passed over a top portion of a door or drawer that is then closed so that when so received the strap second distal end abuts an obverse side of the door or drawer so as to suspend the aperture on the first tab spaced away from the door or drawer.

12. The device of claim 11, wherein the strap is fabricated from a textile material.

13. The device of claim 12 wherein the textile material is continuous.

14. The device of claim 12 wherein the textile material is nylon webbing.

15. The device of claim 11 wherein the acute angle is in a range of 40 to 60 degrees.

16. The device of claim 15 wherein the acute angle is approximately 45 degrees.

17. The device of claim 15 wherein the strap has a length of approximately 14.5", a width of approximately 2", the tabs have a length of approximately one inch each.

18. The device of claim 17 wherein the first leg of the stiffening member has a length of approximately 4" and the second leg has a length of approximately 6".

19. The device of claim 11 wherein the second tab has means for alternatively hanging the device in a second suspension configuration, in which the second tab is hung from a hook without the stiffening member received in the pockets.

20. A method for hanging an infusion fluid bag from a door or drawer, comprising the steps of:
    providing a device having a flexible main body having pockets, the main body further having first and second tabs, the first tab adapted to receive a fluid infusion bag and the second tab adapted to be trapped behind a closed door or drawer;
    providing a removable stiffening member having two legs positioned at an acute angle with respect to one another for receipt in the pockets;
    receiving the stiffening member in the pockets;
    positioning the second tab behind the door or drawer and closing the door or drawer so that the first tab is spaced away from the door or drawer; and
    hanging an infusion fluid bag from the first tab.

* * * * *